(12) United States Patent
Edic

(10) Patent No.: US 6,353,653 B1
(45) Date of Patent: Mar. 5, 2002

(54) METHOD AND APPARATUS FOR REDUCING ARTIFACTS IN IMAGES RECONSTRUCTED FROM IMAGE DATA ACQUIRED BY A COMPUTED TOMOGRAPHY SYSTEM

(75) Inventor: Peter Michael Edic, Albany, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/448,352

(22) Filed: Nov. 23, 1999

(51) Int. Cl.⁷ .............................................. G01N 23/00
(52) U.S. Cl. .................................. 378/8; 378/4; 378/95
(58) Field of Search .................................. 378/4, 8, 95

(56) References Cited

U.S. PATENT DOCUMENTS 5,832,051 A * 11/1998 Lutz ............................... 378/8
6,084,936 A 7/2000 Patch

* cited by examiner

Primary Examiner—Craig E. Church
(74) Attorney, Agent, or Firm—Donald S. Ingraham; Christian G. Cabou

(57) ABSTRACT

A method and apparatus for use with a computed tomography (CT) system that collects CT radiograph data for every view of the CT gantry so that a data set corresponding to all views of the gantry is available for use in reconstructing an image of a patient's heart and coronary vasculature. For each view of the gantry, the CT radiograph data associated with the view is collected at different instants in time with respect to the period of the cardiac cycle in each revolution of the gantry. Prior to data acquisition, the patient's heart rate is measured and the period of the gantry is set such that data is acquired at a different time with respect to the period of the cardiac cycle for every view of the gantry and for each revolution of the gantry. Therefore, for each revolution of the gantry and for each view of the gantry, the instant in time in the period of the cardiac cycle at which any given detector element of the detector array is sampled will be different from the instant in time in the period of the cardiac cycle at which the same detector element was sampled in the previous revolution. After all of the CT radiograph data is collected, the radiographs are processed by an interpolation algorithm that interpolates radiographs to a selected instant in time with respect to the period of the cardiac cycle. A reconstruction algorithm is then used to process and back-project the interpolated radiographs to produce a three-dimensional (3-D) image of the heart and coronary vasculature. The interpolation algorithm may be performed repeatedly to interpolate radiographs back to more than one instant in time, and then corresponding reconstructions may be performed to generate a four-dimensional (4-D) image of the heart and coronary vasculature.

29 Claims, 4 Drawing Sheets

METHOD AND APPARATUS FOR REDUCING ARTIFACTS IN IMAGES RECONSTRUCTED FROM IMAGE DATA ACQUIRED BY A COMPUTED TOMOGRAPHY SYSTEM

BACKGROUND OF THE INVENTION

The invention relates to computed tomography (CT) and, more particularly, to an apparatus and a method for use in a CT system for reconstructing an image with reduced artifacts.

Computed tomography (CT) is a technique that generally involves subjecting a patient to x-rays, acquiring digital x-ray data of a portion of the patient's body, and processing and back-projecting the digital x-ray data to produce an image that is then displayed on a display monitor of the CT system. CT systems typically comprise a gantry, a table, an x-ray tube, an x-ray detector array, a computer and a display monitor. The computer sends commands to controllers of the gantry to cause the controllers to rotate the x-ray tube and/or the detector array at a particular rotational speed. The detector array is usually comprised of either a curved array (third generation CT system) of detector elements or a ring (fourth generation CT system) of detector elements. In the case where a ring of detector elements is used, only the x-ray tube is rotated.

In third and fourth generation CT systems, relative rotational motion is produced between the detector array and the x-ray tube about the patient's body. As this relative rotational motion is produced, the computer controls the data acquisition process performed by the x-ray tube and the detector array to acquire digital x-ray radiographs. The computer then processes and back-projects the digital x-ray radiograph data by performing a reconstruction algorithm and displays the reconstructed CT image on the display monitor.

In current CT systems, in order to appropriately produce CT images of the coronary vasculature, it is necessary to acquire CT radiograph data while the heart is at a certain position that is substantially spatially stationary. This requires that the heart rate of the patient be extremely slow, which is not clinically viable, or that the speed of the gantry be extremely high, which is not technically viable. In the past, a few different techniques have been employed in attempts to solve this problem. One technique, known as prospective gating, uses the ECG (electrocardiogram) signal of the heart to trigger data acquisition by the detector array at points in time when the heart is fairly stationary (typically during diastole) so that the radiographs used to reconstruct the image correspond to instants in time when the heart is fairly stationary. Another technique, known as retrospective gating, measures the ECG signal while acquiring CT radiograph data and then retrospectively selects the data that corresponds to a point in time of the ECG signal when the heart is fairly stationary.

With both of these techniques, only CT radiograph data that corresponds to a certain time interval during which the heart is substantially spatially stationary is used in reconstructing the CT images. Therefore, during reconstruction, both techniques only use CT radiograph data corresponding to limited view angles, i.e., neither technique uses measured CT radiograph data at all view angles of the CT gantry. Also, both techniques use CT radiograph data obtained during a particular window in time as the heart is moving. Consequently, the CT reconstructions may suffer from motion artifacts and/or limited view angle artifacts.

Another disadvantage of these techniques is that they are limited to reconstructing an image of the heart at a particular time interval, which typically corresponds to diastole. Therefore, neither of these techniques are suitable for reconstructing a four-dimensional (AD) representation of a heart (i.e., 3-D spatial and 1-D temporal). It would be desirable to provide a technique by which a reconstructed image of the heart and coronary vasculature could be generated at any point in time during the cardiac cycle. It would also be desirable to provide a technique by which an image of the heart and coronary vasculature could be generated at several points in time during the cardiac cycle for all views of the gantry to thereby enable a 4-D representation of the heart to be generated.

Accordingly, a need exists for a method and apparatus for use in a CT system that enable CT radiograph data corresponding to all views of the gantry to be utilized in performing CT reconstruction so that the occurrence of limited view angle artifacts in reconstructed CT images can be reduced or eliminated. A need also exists for a method and apparatus for use in a CT system that enable reconstruction to be performed at any instant in time during the cardiac cycle so that the occurrence of motion artifacts in the reconstructed CT images can be reduced or eliminated. A need also exists for a method and apparatus for use in a CT system that will enable reconstruction to be performed at several points in time during the cardiac cycle to enable a 3-D or 4-D representation of the heart to be generated.

BRIEF SUMMARY OF THE INVENTION

The present invention provides a method and apparatus for use with a computed tomography (CT) system that collects CT radiograph data for every view of the CT gantry so that a data set corresponding to all views of the gantry is available for use in reconstructing an image of a patient's heart and coronary vasculature. For each view of the gantry, the CT radiograph data associated with the view is collected at different instants in time with respect to the period of the cardiac cycle in each revolution of the gantry.

Prior to data acquisition, the patient's heart rate is measured and the period of the gantry is set such that data is acquired at a different time with respect to the period of the cardiac cycle for every view of the gantry and for each revolution of the gantry. Therefore, for each revolution of the gantry and for each view of the gantry, the instant in time in the period of the cardiac cycle at which any given detector element of the detector array is sampled will be different from the instant in time in the period of the cardiac cycle at which the same detector element was sampled in the previous revolution. After all of the CT radiograph data is collected, the radiographs are processed by an interpolation algorithm that interpolates radiographs to a selected instant in time with respect to the period of the cardiac cycle. A reconstruction algorithm is then used to process and back-project the interpolated radiographs to produce a three-dimensional (3-D) image of the heart and coronary vasculature. The interpolation algorithm may be performed repeatedly to interpolate radiographs back to more than one instant in time, and then corresponding reconstructions may be performed to generate a four-dimensional (4-D) image of the heart and coronary vasculature.

These and other features and advantages of the present invention will become apparent from the following description, drawings and claims.

DETAILED DESCRIPTION OF THE INVENTION

Figure 1:
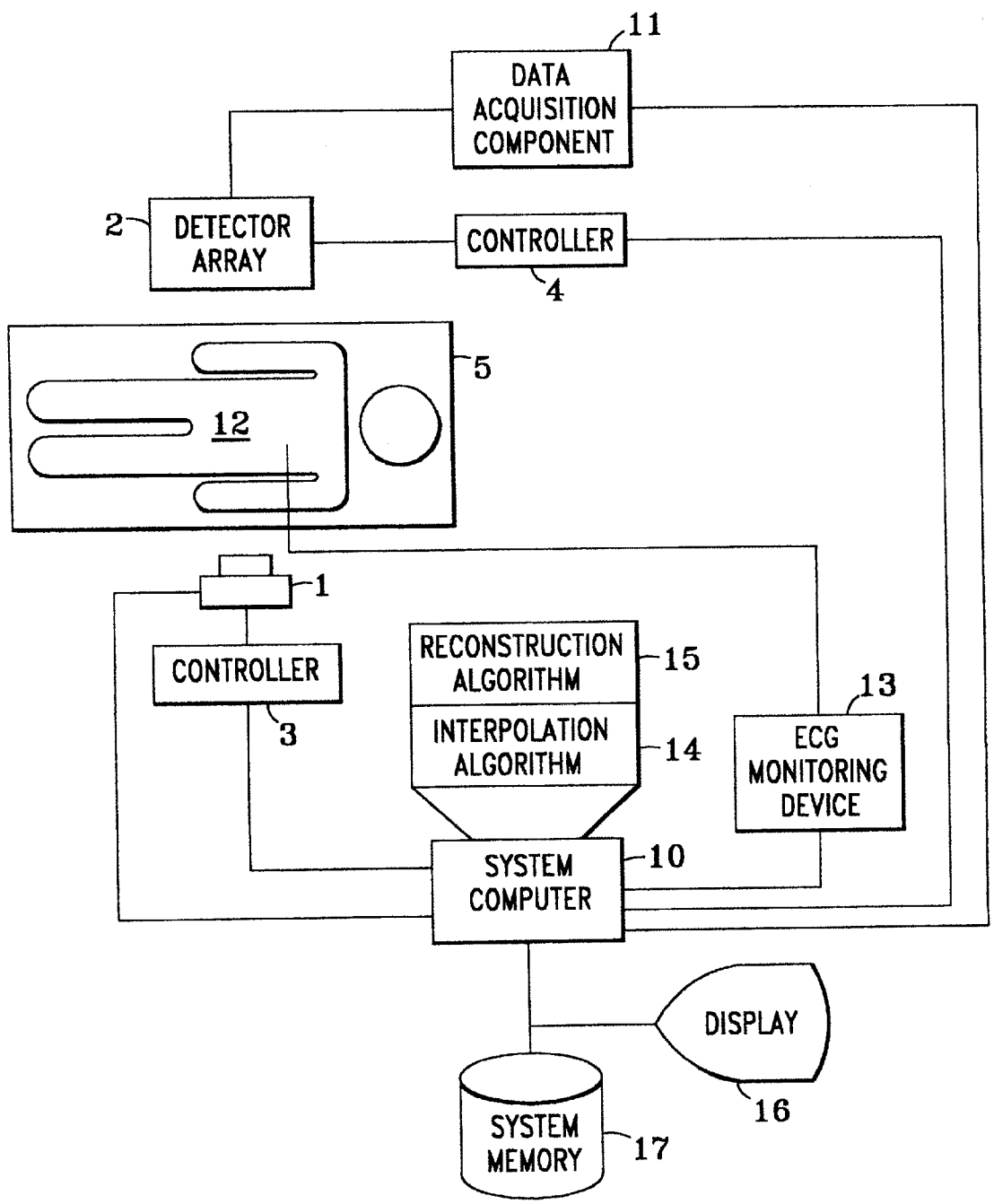
FIG. 1 is a block diagram illustrating the CT system of the present invention in accordance with the preferred embodiment.

FIG. 1 is a block diagram of a typical CT system that is suitable for implementing the method and apparatus of the present invention. The CT system will be discussed with respect to its use in reconstructing an image of a patient's heart and coronary vasculature, although it will be understood that the present invention is not limited to imaging any particular object. In particular, "patient" as used herein refers to any creature to be imaged. The present invention is being described with reference to imaging a patient's heart and coronary vasculature to demonstrate the manner in which the present invention overcomes the difficulties associated with accurately reconstructing an image of a heart and coronary vasculature from data acquired while the heart is beating.

The manner in which a typical CT system is operated is well known in the art. The method and apparatus of the present invention are not limited with respect to the type of CT system with which they are used. The method and apparatus of the present invention preferably are implemented with either a third or fourth generation CT system, since first and second generation CT systems generally are no longer used. As stated above, in the case where the CT system is a fourth generation CT system, the detector array 2 will be a ring detector that remains stationary as the x-ray tube 1 is rotated. The x-ray tube 1 is rotated on a trajectory that is concentric with the ring formed by the ring detector and that may be internal to the ring.

In the case where the CT system is a third generation CT system, both the x-ray tube 1 and the detector array 2 will be rotated while maintaining the alignment between them. With third generation CT systems, the detector array typically is a single-row detector array comprising a single row of detector elements, a multi-row detector array comprising a few rows of detector elements or an area detector comprised of a large number of rows of detector elements. All of these different types of detector arrays are suitable for use with the present invention.

The CT system with which the present invention is utilized may perform a helical tomography protocol. Helical tomography is performed by continuously rotating the x-ray tube 1 and/or the detector array 2 about the gantry while slowly advancing the table 5 through the gantry in order to generate a helical scan. By using helical scanning, the patient area to be imaged can be scanned in a relatively short scan time, typically in one hold-breath of the patient. Using helical scanning also enables the occurrence of motion artifacts in the reconstructed image to be reduced. Also, rather than moving the table 5, data acquisition may be performed by using an area detector as the detector array 2. The area detector is rotated about the patient 12 in order to scan the entire volume of the object being imaged, which eliminates the need for moving the table 5. However, if an area detector is used, it may be necessary to acquire additional data to reduce cone beam artifacts. Those skilled in the art will understand the manner in which any of these CT scanning protocols can be implemented.

As stated above, in typical CT systems, the gantry is rotated at a particular rotational speed about the body of the patient 12. When referring herein to the rotation of the gantry, that phrase is intended to denote rotation of the x-ray tube 1 and/or rotation of the detector array 2, which depends on whether the CT system is a third or fourth generation CT system. The x-ray tube 1 and the detector array 2 are comprised by the gantry. The controllers 3 and 4 are controlled by the CT system computer 10 and are coupled to the x-ray tube 1 and to the detector array 2, respectively. The controllers 3 and 4 cause the appropriate relative rotational motion to be imparted to the x-ray tube 1 and/or to the detector array 2, as well as the speed of rotation of the x-ray tube 1 and/or of the detector array 2. Individual controllers are not necessary. A single controller component may be used to rotate the gantry.

In accordance with the present invention, the speed of the gantry is set such that, for each rotation of the gantry, data is acquired at a different time with respect to the period of the cardiac cycle for any given view of the gantry. For each view of the gantry, the detector array 2 is sampled at different times with respect to the period of the cardiac cycle for each revolution of the gantry occurring during the data acquisition period. A single revolution of the gantry is made up of a particular number of views ranging from view $N_0$ to view $N_x$, where X is a positive integer. Therefore, one revolution of the gantry corresponds to X+1 views acquired by the detector array 2. Typical CT systems utilized for medical imaging acquire roughly 1,000 views per rotation of the gantry, which corresponds to approximately one view every ⅓ of a degree of rotation of the gantry. However, this number is arbitrary and is determined by the CT system design. Therefore, the present invention is not limited with respect to the number of views that make up a full rotation of the gantry.

A single view of the gantry corresponds to a sampling of all of the detector elements of the detector array 2. For each view, the detector array 2 will be sampled multiple times during the data acquisition process (i.e., once per revolution of the gantry) and each sampling will be at a different time with respect to the period of the cardiac cycle. The data acquisition process will occur over multiple cardiac cycles. One hold-breath of the patient may correspond to, for example, 40 cardiac cycles ranging from $cycle_1$ to $cycle_{40}$, with each cycle having a duration equal to a time period $T_{HEART}$ which corresponds to the period of the cardiac cycle. As stated above, for every view of the gantry, each sampling will occur at a different point in time with respect to the period of the cardiac cycle. For example, for view $N_{10}$ of the gantry, a particular detector element of the detector array 2 may be sampled at one particular time in cardiac cycle, during one revolution of the gantry and then at a different time during $cardiac cycle_2$ in the next subsequent revolution of the gantry. This process will continue throughout the data acquisition period until a sufficient number of samples have been obtained for each view of the gantry.

The computer 10 controls the data acquisition process by instructing the data acquisition component 11 as to when to sample the detector array 2. In order to ensure that the samples obtained for any given view are obtained at different times with respect to the period of the cardiac cycle for each revolution of the gantry, the heart rate (beats per second) of the patient 12 is measured and the rotational speed (revolutions per second) of the gantry is set to a rate that is either greater than or less than the heart rate of the patient 12. The heart rate of the patient 12 may be measured by using an ECG monitoring device 13 or by using some other suitable device, such as, for example, a stethoscope (not shown).

As the detector element samples, or radiographs, are acquired, the computer 10 correlates the radiographs with the times that they correspond to in the cardiac cycle as well as with the views of the gantry to which they correspond. The interpolation algorithm 14 of the present invention then generates interpolated radiographs that are then processed and back-projected by the reconstruction algorithm 15 to reconstruct a CT image which is then displayed on display monitor 16. The interpolation algorithm 14 will be discussed in detail below with reference to FIG. 5.

The apparatus of the present invention is comprised of a computer, such as the CT system computer 10, that is configured to perform the interpolation algorithm 14 of the present invention, and a memory device, such as system memory device 17. Preferably, the apparatus of the present invention is comprised of the CT system computer 10 and the system memory device 17. In accordance with one embodiment, the apparatus of the present invention farther comprises the ECG monitoring device 13. When the apparatus of the present invention is incorporated into an existing CT system and is used in conjunction with the interpolation algorithm 14 of the present invention, a new CT system is created. Therefore, the present invention also provides a new CT system that is capable of reconstructing images with reduced artifacts.

Programs and data are stored in the system memory device 17 for use by the computer 10. As discussed below with reference to FIG. 5, the CT radiograph data acquired during the data acquisition process is stored in the memory device 17 or in some other suitable memory device (not shown). The data is read out of the memory device 17 and is utilized by the computer 10 in performing the interpolation and reconstruction algorithms 14 and 15, respectively, as discussed below in detail.

Figure 2:
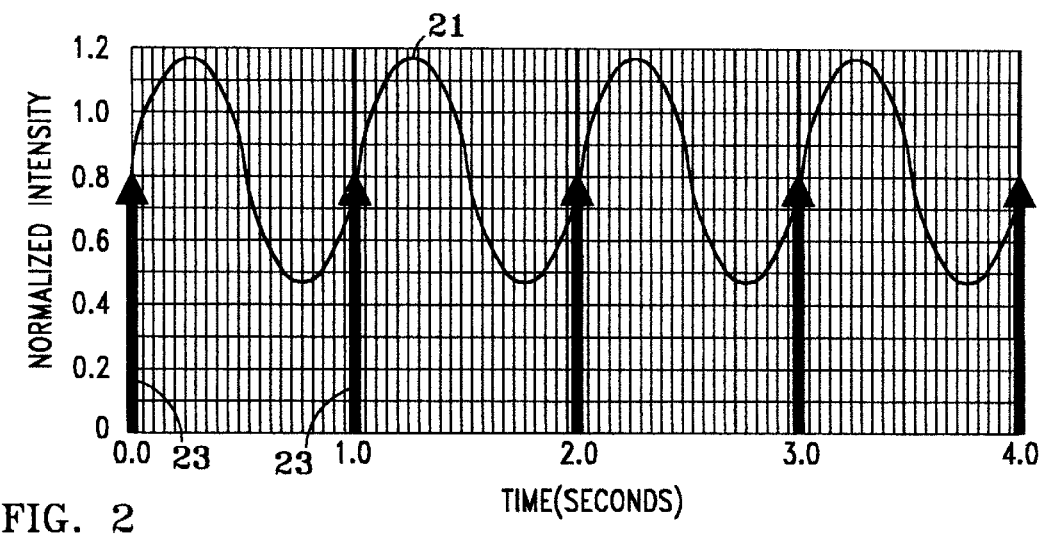
FIG. 2 is a plot of the normalized output intensity of a particular detector element of the detector array shown in FIG. 1 as a function of time over four cardiac cycles, wherein the period of the cardiac cycle is equal to the period of a gentry.

FIG. 2 illustrates a plot of the normalized intensity output of a single detector element for a particular view of the gantry over four cardiac cycles as a function of time. This plot represents the continuous acquisition of data by the detector element while the gantry is maintained in a stationary position. The heart rate is assumed, for illustrative purposes, to be one beat per second. In this example, the rotational speed of the gantry has been set to one rotation per second so that the period of the gantry exactly matches the period of the cardiac cycle. The plot represents CT radiograph data collected over four cardiac cycles. Each cardiac cycle corresponds to one revolution of the gantry.

The arrows 23 correspond to the time at which the particular detector element was sampled for the particular view of the rotating gantry. As demonstrated by FIG. 2, when the rate of rotation of the gantry is equal to the patient's heart rate, the detector element is sampled at the same instant in time in each cardiac cycle for each rotation of the gantry. In accordance with the present invention, in order to ensure that each detector element is sampled at a different instant in time with respect to the period of the cardiac cycle for each rotation of the gantry, the speed of the gantry (revolutions per second) is set so that the rate of rotation of the gantry is either less than or greater than the heart rate (beats per second) of the patient.

Figure 3:
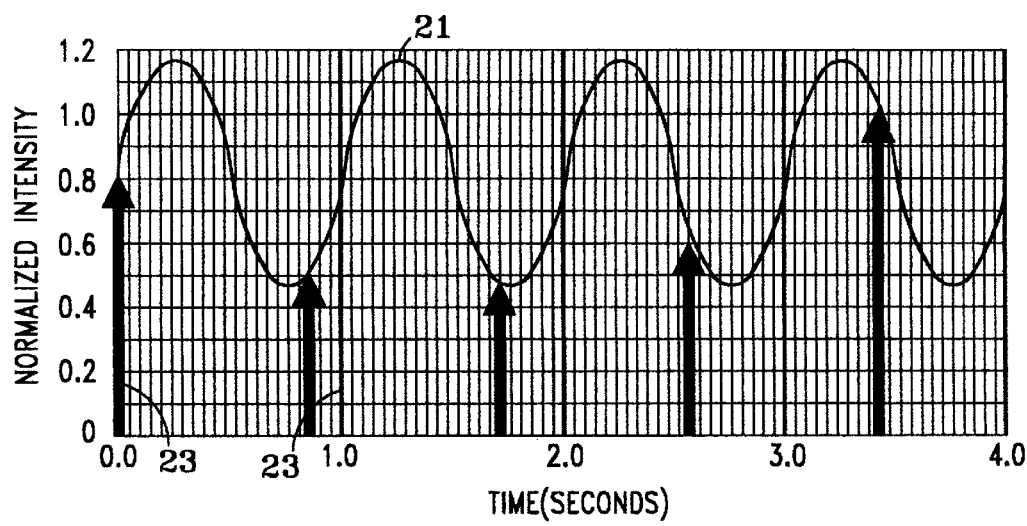
FIG. 3 is a plot of the normalized output intensity of a particular detector element of the detector array shown in FIG. 1 as a function of time over four cycles, wherein the period of the gantry is slightly less than the period of the cardiac cycle.

FIG. 3 illustrates a plot of the normalized intensity output of a particular detector element for four cardiac cycles for a particular view of the gantry wherein the speed of the gantry has been set to a rate of rotation that is slightly greater than the patient's heart rate. This results in the detector element being sampled at a different instant in time with respect to the period of the cardiac cycle in each revolution of the gantry.

Although FIG. 3 illustrates the sampling of the incident x-ray intensity by a single detector element, it should be noted that each detector element of the detector array 2 is simultaneously sampling the incident x-ray intensity at various points in time over the cardiac cycles. Therefore, by the end of the data acquisition process, which preferably occurs during a single breath-hold of the patient (e.g., 40 cardiac cycles), CT radiographs at different points in time with respect to the period of the cardiac cycle have been acquired over a plurality of cardiac cycles by all of the detector elements of the detector array 2 for every view of the gantry.

After the data acquisition process has been completed, the interpolation algorithm 14 of the present invention generates interpolated radiographs corresponding to every view of the CT gantry at a particular instant in time. Therefore, interpolated radiographs corresponding to all of the view angles of the gantry at the particular point in time will be available for use by the reconstruction algorithm 15 performed by the computer 10 to thereby reconstruct a CT image of the heart and coronary vasculature. Since all of the view angles of the gantry are used in the reconstruction, limited view angle artifacts in the reconstructed image will be eliminated. Furthermore, since the reconstruction algorithm 15 performs the reconstruction using interpolated radiographs associated with a particular instant in time, rather than using actual radiographs acquired during a time window, the occurrence of motion artifacts in the reconstructed CT image is also reduced or eliminated.

Figure 4:
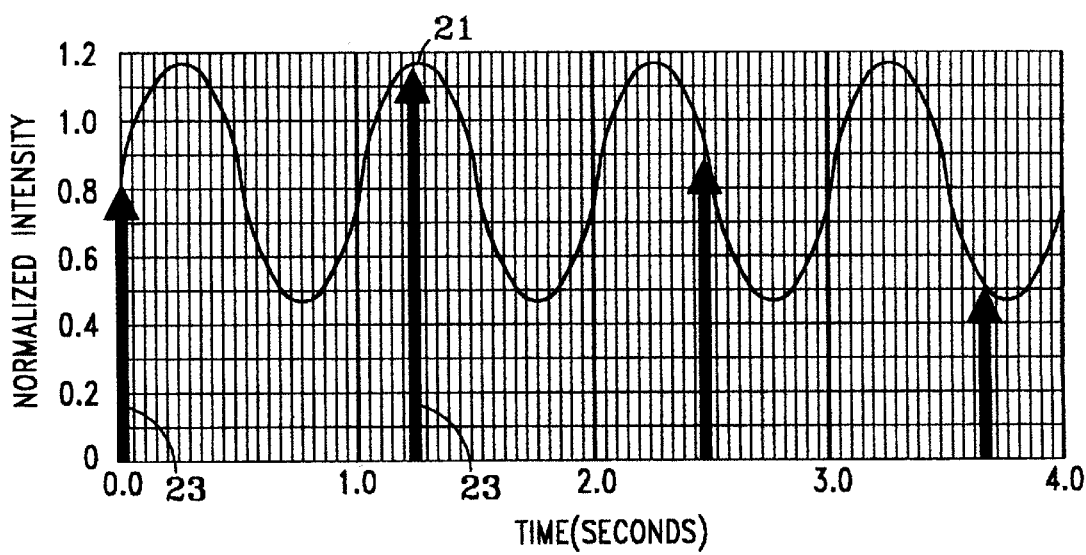
FIG. 4 is a plot of the normalized output intensity of a particular detector element of the detector array shown in FIG. 1 as a function of time over four cycles, wherein the period of the gantry is slightly greater than the period of the cardiac cycle.

FIG. 4 is a plot of the normalized intensity output of one particular detector element of the detector array 2 over four cardiac cycles as a function of time for one particular view of the gantry. For this example, the speed of the gantry (revolutions per second) has been decreased to a rate that is less than the heart rate (beats per second) of the patient. Therefore, the detector element corresponding to the plot acquires samples at different points in time for each cardiac cycle. By applying this technique to all of the detector elements for all views of the gantry, a data set is acquired for all views of the gantry.

FIGS. 3 and 4 demonstrate that the gantry speed can be set to a rotational rate that is either less than or greater than the patient's heart rate. In both cases, for each view of the gantry, each detector element will produce radiograph data that corresponds to a different point in time with respect to the period of the cardiac cycle for each revolution of the gantry occurring during the data acquisition period. This data set can then be interpolated to a particular point in time with respect to the period of the cardiac cycle to enable interpolated radiographs to be generated for every view of the gantry at that particular point in time. This allows the motion of the heart to be "frozen" at one particular instant in time in the cardiac cycle, which enables the occurrence of motion artifacts in the reconstructed image to be eliminated or reduced.

During the data acquisition process, the ECG waveform preferably is measured by the ECG monitoring device 13, although the heart rate could be measured or estimated by some other device. Using the ECG monitoring device 13 to continuously monitor the heart rate enables variations in the heart rate to be detected and taken into account in interpolating the CT radiograph data. The ECG waveform is sampled and stored by the computer 10 in the system memory device 17. The CT radiograph data measured by the detector elements of the detector array 2 are sampled and digitized by the data acquisition component 11 and stored by the computer 10 in the system memory 17. For each sample acquired by a detector element of the detector array 2, the instant in time of the cardiac cycle at which the sample is obtained is recorded in the memory device 17 in such a manner that the sample is associated in memory with the instant in time in the cardiac cycle at which it was obtained. The view angles of the gantry are typically recorded by CT systems as the CT radiograph data is acquired. This enables the samples obtained by the ECG monitoring device 13 and by the detector elements of the detector array 2 to be stored in memory on a view angle basis.

The sampling of the ECG waveform is synchronized to the sampling of the detector elements so that a correspondence exists between the samples obtained by the detector elements and the samples obtained by the ECG monitoring device 13. Therefore, once the data acquisition process has been completed, the system memory device 17 will contain a record of the intensity values obtained by each detector element of the detector array 2 and the instant in time in the cardiac cycle at which the particular sample was obtained, as well as the view angle to which the CT radiograph data corresponds.

Figure 5:
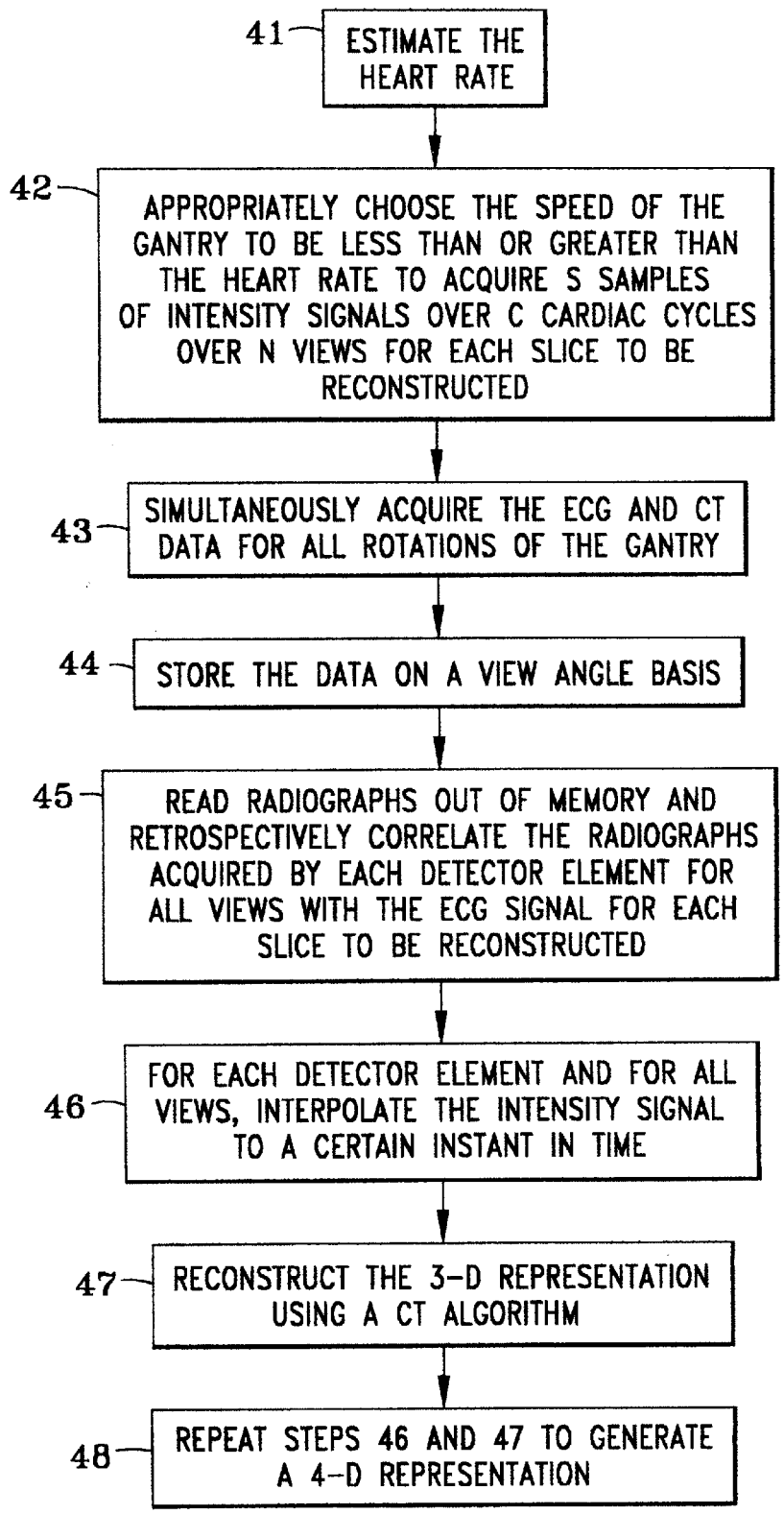
FIG. 5 is a flow chart illustrating the method of the present invention in accordance with the preferred embodiment.

FIG. 5 is a flow chart illustrating the method of the present invention in accordance with the preferred embodiment. The first step of the method of the present invention is to estimate the heart rate of the patient 12, as indicated by block 41. The cardiac cycle can be estimated by using the ECG monitoring device 13 to measure the patient's heart rate. The speed of the gantry (revolutions per second) is then selected to be either less than or greater than the heart rate of the patient, as indicated by block 42. The data acquisition period is also defined in this step such that S samples of intensity signals over C cardiac cycles will be obtained for each of N views. This will be done for each slice to be reconstructed. When the gantry is rotating at the chosen speed, the computer 10 causes the detector elements of the detector array 2 to be sampled while simultaneously causing the ECG signal to be sampled, as indicated by block 43. As the computer 10 acquires the CT radiograph data and the ECG data, the computer 10 stores the CT radiograph data and the ECG data in memory device 17 on a view angle basis, as indicated by block 44.

Once the intensity signals have been acquired over all cardiac cycles for all view angles and the CT radiograph data and the ECG data have been stored in memory device 17, the computer 10 reads out and processes the stored CT radiograph and ECG data to retrospectively determine which samples of the detector elements at each instant of the ECG waveform correspond to the views of the gantry for each slice to be reconstructed, as indicated by block 45. Therefore, this step determines which detector element samples stored in memory device 17 correspond to which views of the gantry as well as the points in time that the samples correspond to with respect to the cardiac cycle.

Once the radiographs have been correlated to their respective views and to the timing of the ECG waveform, the radiographs are interpolated to a particular instant in time with respect to the period of the cardiac cycle, as indicated by block 46. In essence, the radiographs obtained at the discrete points in time are converted into a continuous-time representation and, from the continuous-time representation, radiographs are interpolated at a particular instant in time with respect to the period of the cardiac cycle. Those skilled in the art will understand the manner in which samples obtained at discrete points in time can be converted into any one of several various types of continuous-time representations and how values can be interpolated from the continuous-time representations using suitable interpolation algorithms.

Generally, the well known Nyquist Theorem provides that, if a sufficient number of discrete samples of a waveform are obtained, a continuous-time representation of the discrete-time waveform can be generated and the value of any sample along the continuous-time representation can be interpolated at any point in time by selecting the sample value on the continuous-time representation that corresponds to the point in time. For example, a Fourier time series is a suitable continuous-time function for this purpose. Those skilled in the art will understand that a variety of algorithms are available that are suitable for generating such a continuous-time representation from the discrete-time representation and for interpolating sample values using the continuous-time representation.

Once the radiographs corresponding to all of the views of the gantry have been interpolated to a particular instant in time for each of the detector elements for all views of the gantry, an 3-D image of the heart and coronary vasculature may be reconstructed using, for example, a conventional CT reconstruction algorithm, as indicated by block 47. It will be understood by those skilled in the art that a number of CT reconstruction algorithms are suitable for this purpose. The CT reconstruction algorithm 15 utilized for this purpose can be a known CT reconstruction algorithm or a proprietary CT reconstruction algorithm. The CT reconstruction algorithm does not need to be modified to handle the interpolated radiographs. The CT reconstruction algorithm simply receives the interpolated radiographs and processes them in the normal manner. Therefore, the present invention is not limited with respect to the CT reconstruction algorithm that is used to reconstruct the CT images.

As an alternative to choosing a rate of rotation of the gantry that is either less than or greater than the heart rate of the patient, the speed of the gantry could be continuously adjusted in such a manner that data is acquired at a different time of the cardiac cycle for every view of the gantry and for each rotation of the gantry. However, if the speed of the gantry is continuously adjusted, additional steps must be taken to record the angular view position of the gantry along with the ECT data and the CT radiograph data. Those skilled in the art will understand the manner in which this alternative step could be performed.

It should also be noted that it is not necessary to acquire the ECG signal simultaneously with the detector samples. Rather, the heart rate can be measured prior to the data acquisition process being performed and then the period of the cardiac cycle can be estimated. In this case, as the detector samples are acquired, the occurrence of the detector samples in time with respect to the estimated heart rate will be recorded in the memory device 17 on a view angle bas is. T he CT radiograph data can then be interpolated and reconstructed in the aforementioned manner. This alternative technique is satisfactory where the heart rate does not vary, but may present difficulties in situations where the heart rate does vary. Therefore, it is preferable to sample the ECG signal during the data acquisition process so that the detector element samples can be precisely correlated in time with respect to the period of the cardiac cycle.

It should also be noted that by repeating the steps represented by blocks 46 and 47, reconstructions performed using interpolated radiographs at one or more different times during the cardiac cycle can be performed to generate a 4-D model of the heart (i.e., 3-D spatial and 1-D temporal), as indicated by block 48. By repeatedly performing the steps represented by blocks 46 and 47 the 3-D image can be generated at one or more points in time to produce a 4-D representation.

Several different CT systems and data acquisition protocols can be used to acquire the radiograph data that is then processed using the interpolation algorithm 14. For example, a single-slice CT system that uses a detector array comprising a single row of detector elements, a multi-row helical CT system that uses a detector array comprising a few rows of detector elements, or a volumetric CT system that uses an area detector comprising hundreds of rows of detector elements. Any of these CT systems can be used to acquire the necessary CT radiograph data. The data acquisition protocol will be different in each of these cases. Those skilled in the art will understand the manner in which any of these types of CT systems may be used to acquire the necessary CT radiograph data. Therefore, a detailed discussion of these systems and the manner in which they are operated will not be provided herein in the interest of brevity.

Preferably, the CT system that incorporates the method and apparatus of the present invention is a volumetric CT system comprising an area detector . Employing the area detector allows the necessary CT radiograph data to be collected over the entire axial extent of the heart in only a few cardiac cycles. It is not necessary to move the patient table since the CT radiograph data is measured over the complete extent of the heart with the area detector.

As stated above, the method of the present invention preferably is performed in software executed by the CT system computer 10. However, it is not necessary that the interpolation algorithm 14 of the present invention be performed by the CT system computer 10. Rather, a separate computer (not shown) may be used for performing the interpolation algorithm 14 and the reconstruction algorithm 15. Similarly, any suitable memory device may be used for storing the detector samples and the ECG samples. Therefore, it is not necessary that these samples be stored in the system memory 17.

It should also be noted that the present invention is not limited to any particular computer for performing the data acquisition and processing tasks of the present invention. The term "computer", as that term is used herein, is intended to denote any machine capable of performing the calculations, or computations, necessary to perform the tasks of the present invention. Therefore, the computer utilized to perform the interpolation algorithm 14 of the present invention can be any machine that is capable of performing the necessary tasks.

It should be noted that the present invention has been described with respect to the preferred embodiments and that the present invention is not limited to these embodiments. Those skilled in the art will also understand that the present invention is not limited with respect to the type of CT system with which the present invention is implemented. It should also be noted that the present invention is not limited with respect to the total number of samples that are taken, the number of cardiac cycles over which the data acquisition process is performed, or with respect to the number of samples for any given detector element that are taken during any given cardiac cycle. Those skilled in the art will understand that modifications can be made to the embodiments discussed above without deviating from the spirit and scope of the present invention.

What is claimed is:

1. A computed tomography (CT) system for imaging a patient comprising:

a gantry comprising an x-ray tube and a detector array, the x-ray tube generating x-rays, the detector array receiving x-rays emitted by the x-ray tube, the detector array comprising a plurality of detector elements, each detector element generating an output signal in response to x-rays impinging thereon;

a support surface adapted to receive and support a patient;

a controller component in communication with the gantry, the controller component being capable of producing relative rotational motion between the x-ray tube and the detector array about the support surface, wherein 360° of relative rotational motion corresponds to a revolution of the gantry, each revolution of the gantry corresponding to a plurality of views of the gantry, the patient having a heart rate, the heart rate being associated with a cardiac cycle, the cardiac cycle having a period;

a data acquisition component in communication with the detector array, the data acquisition component being capable of sampling the detector elements by reading and digitizing the output signals generated by the detector elements; and a computer in communication with the controller component and with the data acquisition component, the computer causing the data acquisition component to sample the detector elements at least once for each view of the gantry, wherein for each revolution of the gantry, each detector element is sampled at a different instant in time with respect to the period of the cardiac cycle for each view of the gantry.

2. The CT system of claim 1, wherein the revolutions of the gantry occur at a rotational rate that is greater than or less than an estimated heart rate of the patient, the CT system further comprising:

an electrocardiogram (ECG) monitoring device that monitors the heart rate of the patient and produces an ECG waveform corresponding to the cardiac cycle of the patient, the ECG monitoring device being in communication with the computer, the computer obtaining digital samples of the ECG waveform from the ECG monitoring device simultaneously as the data acquisition component samples the detector elements, the computer processing ECG waveform samples to estimate the period of the cardiac cycle;

a memory device in communication with the computer, the computer storing the detector element samples and the ECG waveform samples at locations in the memory device, the detector element samples corresponding to radiograph data, wherein each detector element sample is associated in the memory device with a particular ECG waveform sample and with a particular view of the gantry, and wherein for each view of the gantry, the computer correlates the stored radiograph data with the stored samples of the ECG waveform for each view of the gantry, the computer performing an interpolation algorithm that processes the correlated radiograph data to interpolate radiograph data to a single instant in time with respect to the period of the cardiac cycle, the computer processing the interpolated radiograph data to reconstruct an image of the patient's heart at the single instant in time; and a display device, the reconstructed image being displayed on the display device.

3. The CT system of claim 1, wherein the revolutions of the gantry occur at a rotational rate that is greater than or less than an estimated heart rate of the patient, the computer utilizing the estimated heart rate to correlate the detector element samples in time with respect to the period of the cardiac cycle, the period of the cardiac cycle being associated with the estimated heart rate, the CT system further comprising:

a memory device in communication with the computer, the computer storing the time-correlated detector element samples, the detector element samples corresponding to radiograph data, wherein the radiograph data is associated in the memory device with a particular instant in the cardiac cycle and with a particular view of the gantry, and wherein for each view of the gantry, the computer processes the correlated radiograph data to interpolate radiograph data to a single instant in time with respect to the period of the cardiac cycle, the computer processing the interpolated radiograph data to reconstruct an image of the patient's heart at the single instant in time; and a display device, the reconstructed image being displayed on the display device.

4. The CT system of claim 2, wherein the rotational rate of the gantry is set to a rate that is greater than the heart rate of the patient.

5. The CT system of claim 2, wherein the rotational rate of the gantry is set to a rate that is less than the heart rate of the patient.

6. The CT system of claim 2, wherein the computer processes the correlated radiograph data to interpolate radiographs to a plurality of instants in time with respect to the cardiac cycle, the computer processing the interpolated radiographs to reconstruct an image of the patient's heart at each of the plurality of instants in time to thereby reconstruct a 3-D representation of the patient's heart that changes as a function of time.

7. The CT system of claim 2, wherein the computer reconstructs the image by performing a reconstruction algorithm that processes and back-projects the radiographs.

8. The CT system of claim 2, wherein the CT system utilizes a helical scanning protocol.

9. The CT system of claim 2, wherein the CT system is a single-slice CT system.

10. The CT system of claim 2, wherein the CT system is a multi-row helical CT system.

11. The CT system of claim 2, wherein the CT system is a volumetric CT system and wherein the detector array is an area detector.

12. A method for acquiring radiograph data in a computed tomography (CT) system, the CT system comprising a gantry, the gantry comprising an x-ray tube and a detector array, the x-ray tube generating x-rays, the detector array receiving x-rays emitted by the x-ray tube, the detector array comprising a plurality of detector elements, each detector element generating an output signal in response to x-rays impinging thereon, the method comprising the steps of:

measuring a heart rate of a patient, the heart rate being associated with a cardiac cycle, the cardiac cycle having a period;

producing relative rotational motion between the x-ray tube and the detector array about a support surface, wherein 360° of relative rotational motion corresponds to a revolution of the gantry, each revolution of the gantry corresponding to a plurality of views of the gantry; and sampling the detector elements by reading and digitizing the output signals generated by the detector elements, the detector elements being sampled at least once for each view of the gantry, and wherein for each revolution of the gantry, each detector element is sampled at a different instant in time with respect to the period of the cardiac cycle for each view of the gantry.

13. A method for reducing artifacts in images reconstructed from image data acquired by a computed tomography (CT) system, the method comprising the steps of:

measuring a heart rate of a patient, the heart rate being associated with a cardiac cycle, the cardiac cycle having a period;

producing relative rotational motion between the x-ray tube and the detector array about a support surface, wherein 360° of relative rotational motion corresponds to a revolution of the gantry, each revolution of the gantry corresponding to a plurality of views of the gantry, wherein the revolutions of the gantry occur at a rotational rate that is greater than or less than the measured heart rate of the patient; and sampling the detector elements by reading and digitizing the output signals generated by the detector elements, the detector elements being sampled at least once for each view of the gantry, and wherein for each revolution of the gantry, each detector element is sampled at a different instant in time with respect to the period of the cardiac cycle for each view of the gantry;

monitoring the heart rate of the patient with an electrocardiogram (ECG) monitoring device, the ECG monitoring device producing an ECG waveform corresponding to the cardiac cycle of the patient;

obtaining digital samples of the ECG waveform from the ECG monitoring device simultaneously as the detector elements are sampled;

storing the detector element samples and the ECG waveform samples at locations in a memory device such that each detector element sample is associated in the memory device with a particular ECG waveform sample and with a particular view of the gantry, the detector element samples corresponding to radiograph data;

reading the radiograph data and the ECG waveform samples out of the memory device and, for each view of the gantry, correlating the radiograph data associated with the view with the ECG waveform samples associated with the radiograph data;

processing the correlated radiograph data to interpolate radiograph data to a single instant in time with respect to the period of the cardiac cycle; and processing the interpolated radiograph data to reconstruct a 3-D image of the patient's heart at the single instant in time.

14. The method of claim 13, further comprising the step of:

displaying the reconstructed image on a display device.

15. The method of claim 13, wherein the rotational rate of the gantry is set to a rate that is greater than the heart rate of the patient.

16. The method of claim 13, wherein the rotational rate of the gantry is set to a rate that is less than the heart rate of the patient.

17. The method of claim 13, wherein the interpolation step includes the step of interpolating the radiograph data to a plurality of instants in time with respect to the period of the cardiac cycle, and wherein the step of processing the interpolated radiograph data includes the step of processing the interpolated radiograph data to reconstruct an image of the patient's heart at each of said plurality of instants in time to thereby reconstruct a 3-D representation of the patient's heart that changes as a function of time.

18. The method of claim 13, wherein the step of processing the interpolated radiograph data to reconstruct the image is performed by a known reconstruction algorithm that processes and back-projects the radiograph data, the reconstruction algorithm being executed by a computer of the CT system.

19. The method of claim 13, wherein the step of interpolating radiograph data is performed by an interpolation algorithm being executed by said computer of the CT system.

20. A computer program for reducing artifacts in images reconstructed from image data acquired by a computed tomography (CT) system, the CT system comprising a gantry, the gantry comprising an x-ray tube and a detector array, the x-ray tube generating x-rays, the detector array receiving x-rays emitted by the x-ray tube, the detector array comprising a plurality of detector elements, each detector element generating an output signal in response to x-rays impinging thereon, the computer program being embodied on a computer-readable medium, the program comprising:

a first code segment for causing relative rotational motion to be produced between the x-ray tube and the detector array about a support surface, wherein 360° of relative rotational motion corresponds to a revolution of the gantry, each revolution of the gantry corresponding to a plurality of views of the gantry, the revolutions of the gantry occurring at a rotational rate that is greater than or less than a measured heart rate of a patient, the heart rate being associated with a cardiac cycle, the cardiac cycle having a period; and a second code segment for causing the detector elements to be sampled, the detector elements being sampled by reading and digitizing the output signals generated by the detector elements, the detector elements being sampled at least once for each view of the gantry, wherein for each revolution of the gantry, each detector element is sampled at a different instant in time with respect to the period of the cardiac cycle for each view of the gantry.

21. The computer program of claim 20, further comprising:

a third code segment for causing an ECG monitoring device to be sampled, the ECG monitoring device monitoring the heart rate of the patient, the ECG monitoring device producing an ECG waveform corresponding to the cardiac cycle of the patient, the third code segment causing digital samples of the ECG waveform to be obtained from the ECG monitoring device simultaneously as the detector elements are sampled;

a fourth code segment for storing the detector element samples and the ECG waveform samples at locations in a memory device such that each detector element sample is associated in the memory device with a particular ECG waveform sample and with a particular view of the gantry, the detector element samples corresponding to radiograph data;

a fifth code segment that reads the radiograph data and the ECG waveform samples out of the memory device and correlates the radiograph data associated with each view of the gantry with the associated ECG waveform samples;

a sixth code segment for processing the correlated radiograph data to interpolate radiograph data to a single instant in time with respect to the period of the cardiac cycle; and a seventh code segment that uses the interpolated radiograph data to reconstruct an image of the patient's heart at the single instant in time.

22. The computer program of claim 21, further comprising:

an eighth code segment for causing the reconstructed image to be displayed on a display device.

23. An apparatus for use in a computed tomography (CT) system for acquiring radiograph data to be used by the CT system, the CT system comprising a gantry, a support table a controller component, and a data acquisition component, the gantry comprising an x-ray tube and a detector array, the x-ray tube generating x-rays, the detector array receiving x-rays emitted by the x-ray tube, the detector array comprising a plurality of detector elements, each detector element generating an output signal in response to x-rays impinging thereon, the support surface being adapted to receive and support a patient, the controller component being in communication with the gantry and being capable of producing relative rotational motion between the x-ray tube and the detector array about the support surface, wherein 360° of relative rotational motion corresponds to a revolution of the gantry, each revolution of the gantry corresponding to a plurality of views of the gantry, the patient having a heart rate associated with a cardiac cycle, the cardiac cycle having a period, the data acquisition component being in communication with the detector array and being capable of sampling the detector elements by reading and digitizing the output signals generated by the detector elements, the apparatus comprising:

a computer in communication with the controller component and with the data acquisition component, the computer causing the data acquisition component to sample the detector elements at least once for each view of the gantry, wherein for each revolution of the gantry, each detector element is sampled at a different instant in time with respect to the period of the cardiac cycle for each view of the gantry.

24. The apparatus of claim 23, wherein the apparatus uses the acquired radiograph data to produce reconstructed images, and wherein the revolutions of the gantry occur at a rotational rate that is greater than or less than an estimated heart rate of the patient, the apparatus further comprising:

an electrocardiogram (ECG) monitoring device that monitors the heart rate of the patient and produces an ECG waveform corresponding to the cardiac cycle of the patient, the ECG monitoring device being in communication with the computer, the computer obtaining digital samples of the ECG waveform from the ECG monitoring device simultaneously as the data acquisition component samples the detector elements; and a memory device in communication with the computer, the computer storing the detector element samples and the ECG waveform samples at locations in the memory device, the detector element samples corresponding to radiograph data, wherein each detector element sample is associated in the memory device with a particular ECG waveform sample and with a particular view of the gantry, and wherein for each view of the gantry, the computer reading the radiograph data and the ECG waveform samples out of the memory device and correlating the radiograph data with the samples of the ECG waveform for each view of the gantry, the computer performing an interpolation algorithm that processes the correlated radiograph data to interpolate radiograph data to a single instant in time with respect to the period of the cardiac cycle, the computer processing the interpolated detector element samples to reconstruct an image of the patient's heart at the single instant in time.

25. The apparatus of claim 23, wherein the revolutions of the gantry occur at a rotational rate that is greater than or less than an estimated heart rate of the patient, the computer utilizing the estimated heart rate to correlate the detector element samples in time with respect to the period of the cardiac cycle, the period of the cardiac cycle being determined by the computer based on the estimated heart rate, the apparatus further comprising:

a memory device in communication with the computer, the computer storing the time-correlated detector element samples, the detector element samples corresponding to radiograph data, wherein the radiograph data is associated in the memory device with a particular instant in the cardiac cycle and with a particular view of the gantry, and wherein for each view of the gantry, the computer processes the correlated radiograph data to interpolate radiograph data to a single instant in time with respect to the period of the cardiac cycle, the computer processing the interpolated radiograph data to reconstruct an image of the patient's heart at the single instant in time.

26. The apparatus of claim 24, wherein the rotational rate of the gantry is set to a rate that is greater than the heart rate of the patient.

27. The apparatus of claim 24, wherein the rotational rate of the gantry is set to a rate that is less than the heart rate of the patient.

28. The apparatus of claim 24, wherein the computer processes the correlated radiograph data to interpolate radiograph data to a plurality of instants in time with respect to the cardiac cycle, the computer processing the interpolated radiograph data corresponding to said plurality of instants in time to reconstruct an image of the patient's heart at each of said plurality of instants in time to thereby reconstruct a 3-D representation of the patient's heart that changes as a function of time.

29. An apparatus for reducing artifacts in images reconstructed from image data acquired by a computed tomography (CT) system, the apparatus comprising:

a computer, the computer obtaining detector element samples and ECG waveform samples from address locations in a memory device, the detector element samples corresponding to radiograph data, the computer correlating the radiograph data with the samples of the ECG waveform for each view of a gantry of a CT system, the computer performing an interpolation algorithm that processes the correlated radiograph data to interpolate radiograph data to a single instant in time with respect to the period of the cardiac cycle, the computer processing the interpolated detector element samples to reconstruct an image of the patient's heart at the single instant in time.

* * * * *